(12) United States Patent
Callueng

(10) Patent No.: US 6,874,697 B2
(45) Date of Patent: Apr. 5, 2005

(54) DEVICE FOR DISINFECTING DOOR HANDLES

(76) Inventor: Ronel Domingo Callueng, 2022 Harwyn Rd., Wilmington, DE (US) 19810

( * ) Notice: Subject to any disclaimer, the term of this patent is extended or adjusted under 35 U.S.C. 154(b) by 93 days.

(21) Appl. No.: 10/602,130

(22) Filed: Jun. 24, 2003

(65) Prior Publication Data

US 2004/0026530 A1 Feb. 12, 2004

Related U.S. Application Data

(60) Provisional application No. 60/401,301, filed on Aug. 6, 2002.

(51) Int. Cl.[7] .................. B05B 17/00; A01G 27/00; B67D 5/08; E03D 9/02
(52) U.S. Cl. ............... 239/1; 239/69; 239/71; 239/302; 4/222; 222/52; 222/644; 422/28; 422/300
(58) Field of Search ............... 239/1, 69, 71, 239/302, 70, 72, 273, 332, 548; 4/222, 228.1; 222/52, 644, 63, 181.3, 651; 422/28, 300, 3, 62, 292

(56) References Cited

U.S. PATENT DOCUMENTS

| | | | |
|---|---|---|---|
| 1,491,780 A | 4/1924 | Abbott | |
| 1,783,097 A | 11/1930 | Polcari | |
| 2,527,955 A | 10/1950 | Pagel | 21/61 |
| 3,314,746 A | 4/1967 | Millar | 21/102 |
| 4,171,776 A | 10/1979 | Pagliaro | 239/274 |
| 4,832,942 A | 5/1989 | Crace | 428/40 |
| 5,016,781 A | 5/1991 | Ten Wolde | 222/162 |
| 5,031,252 A * | 7/1991 | Oyama | 4/233 |
| 5,314,668 A * | 5/1994 | Biermaier | 422/292 |
| 5,695,091 A * | 12/1997 | Winings et al. | 222/1 |
| 5,808,553 A | 9/1998 | Cunningham | 340/573 |
| 6,123,268 A * | 9/2000 | Chastine | 239/1 |
| 6,279,777 B1 * | 8/2001 | Goodin et al. | 222/52 |
| 6,298,521 B1 | 10/2001 | Butterfield | 16/412 |
| 6,645,435 B2 * | 11/2003 | Dawson et al. | 422/110 |

\* cited by examiner

Primary Examiner—Michael Mar
Assistant Examiner—Darren Gorman
(74) Attorney, Agent, or Firm—Jeffrey C. Lew

(57) ABSTRACT

A device for disinfecting door handles and knobs comprising a dispenser for soap or disinfectant adapted to spray the soap or disinfectant on the door handles or knobs when triggered by the motion of a hand.

17 Claims, 5 Drawing Sheets

DEVICE FOR DISINFECTING DOOR HANDLES

This application claims the benefit of U.S. Provisional Application No. 60/401,301 filed Aug. 6, 2002.

FIELD OF THE INVENTION

This invention relates to sanitizing devices for disinfecting door handles and knobs, particularly to devices for spraying disinfecting agent on door handle surfaces.

BACKGROUND OF THE INVENTION

It is well known that bacteria and other microorganisms are the cause of many diseases and are easily transmitted from infected individuals to other persons if sanitary conditions are not maintained where such microorganisms thrive. Restrooms are places where bacteria, viruses and other disease-producing substances are found in great numbers. Indeed in public bathrooms the problem is particularly severe because these facilities are designed to dispose of large volumes of human waste, which contains up to 30% bacteria. It is not unusual to find disease causing organisms on a variety of surfaces in bathrooms, e.g., toilet seats, urinal and commode flush handles, faucet handles, door knobs, push plates, etc. Urine, feces, and other body wastes which contain disease organisms can easily be left on such surfaces, usually by hand transmission. However, germs, particularly fecal bacteria, can also be sprayed into the air when a toilet flushes.

Individuals using bathrooms can protect themselves from these organisms by thorough washing and drying of their hands. However the benefits of hand washing can be negated by subsequent contact with infected door handles when leaving the bathroom. The usual method of reducing microbiological activity on the surfaces of door handles is to spray or wipe them with strong disinfectant. However, this is inconvenient to do on a continuous basis, and a periodic wiping or spraying is not sufficient.

A variety of methods to sanitize door knobs has been described. U.S. Pat. No. 1,783,097, is directed to a hollow door knob carrying disinfectant in its interior and having perforations distributed over its shell for the escape of portions of the disinfectant from the inside portion of the knob to its outside surface.

U.S. Pat. No. 3,314,746, is directed an ultraviolet light built into a door knob or door handle to irradiate the handle with ultraviolet light.

U.S. Pat. No. 1,491,780 describes a hollow door knob equipped with provision for receiving and holding a quantity of crystalline substance in a more or less comminuted form, adapted to slowly and gradually give off a vapor or mist capable of disinfecting and sterilizing the handle.

U.S. Pat. No. 2,527,955 reveals push plates or knobs containing either a cavity within the door stile covered by a pushplate filled with a fluid absorbing sponge of cellulosic material which is impregnated with a slowly evaporating disinfectant, or a hollow door knob provided with such material for the purpose of disinfecting same. The hollow door knob contains a plurality of openings in its surface to permit the escape of the disinfectant fluid or vapor.

U.S. Pat. No. 4,171,776 discloses a door mounted actuating device for use with a spray container of the type having a spray nozzle which when depressed causes a spray of fluid to be emitted from the container. The actuating mechanism permits the unit to spray upon opening or closing the door.

U.S. Pat. No. 4,832,942 is directed to a touch effective disinfectant tape suitable for mounting on a door knob or handle of a bathroom, enabling users to disinfect their hands during the use of such facility.

U.S. Pat. No. 6,298,521 discloses a housing containing a sublimable disinfectant, the housing having an adhesive on the rear end for securing it to the backing plate behind a door knob. The housing has circumferential slots in the front end so that the sublimable disinfectant vapors may reach the door knob.

There is a continuing need to provide an improved and simple device and method for disinfecting door handles and knobs, particularly those present on lavatory doors.

SUMMARY OF THE INVENTION

The present invention thus provides a device for disinfecting a handle of a door comprising:

a) a housing adapted to be mounted on the door, b) a source of electrical energy operative to supply power to the device, c) a vessel in the housing, adapted to contain a liquid comprising soap or disinfectant material, d) a handle operation sensor in the housing effective to detect whether a the handle is in current operation by a human hand, e) a nozzle adapted to form an aerosol of the liquid and a spray of the aerosol onto said door handle, f) an electrically powered pump in the housing and being operative to pump the liquid from the vessel to the nozzle, and g) a controller effective to activate and deactivate the pump.

There is also provided an improved method for disinfecting door handles and knobs comprising the steps of:

(I) providing a device comprising a) a vessel containing a liquid comprising soap or disinfectant material, b) a handle operation sensor effective to detect whether a human hand is currently operating the handle, c) a nozzle adapted to form an aerosol of the liquid, and d) a controller effective to start and stop flow through the nozzle, (II) continuously scanning the handle by the handle operation sensor, (III) transmitting to the controller a handle-in-use signal while the sensor detects that the handle is currently being manipulated by a human hand and a handle-clear signal while the sensor detects that the handle is currently not being manipulated by a hand, (IV) spraying the aerosol from the nozzle onto the door handle for a preselected duration after each time that the controller first receives a handle-clear signal, and (V) stopping the spraying at all times that the controller receives a handle-in-use signal.

DETAILED DESCRIPTION OF THE INVENTION

Figure 1:
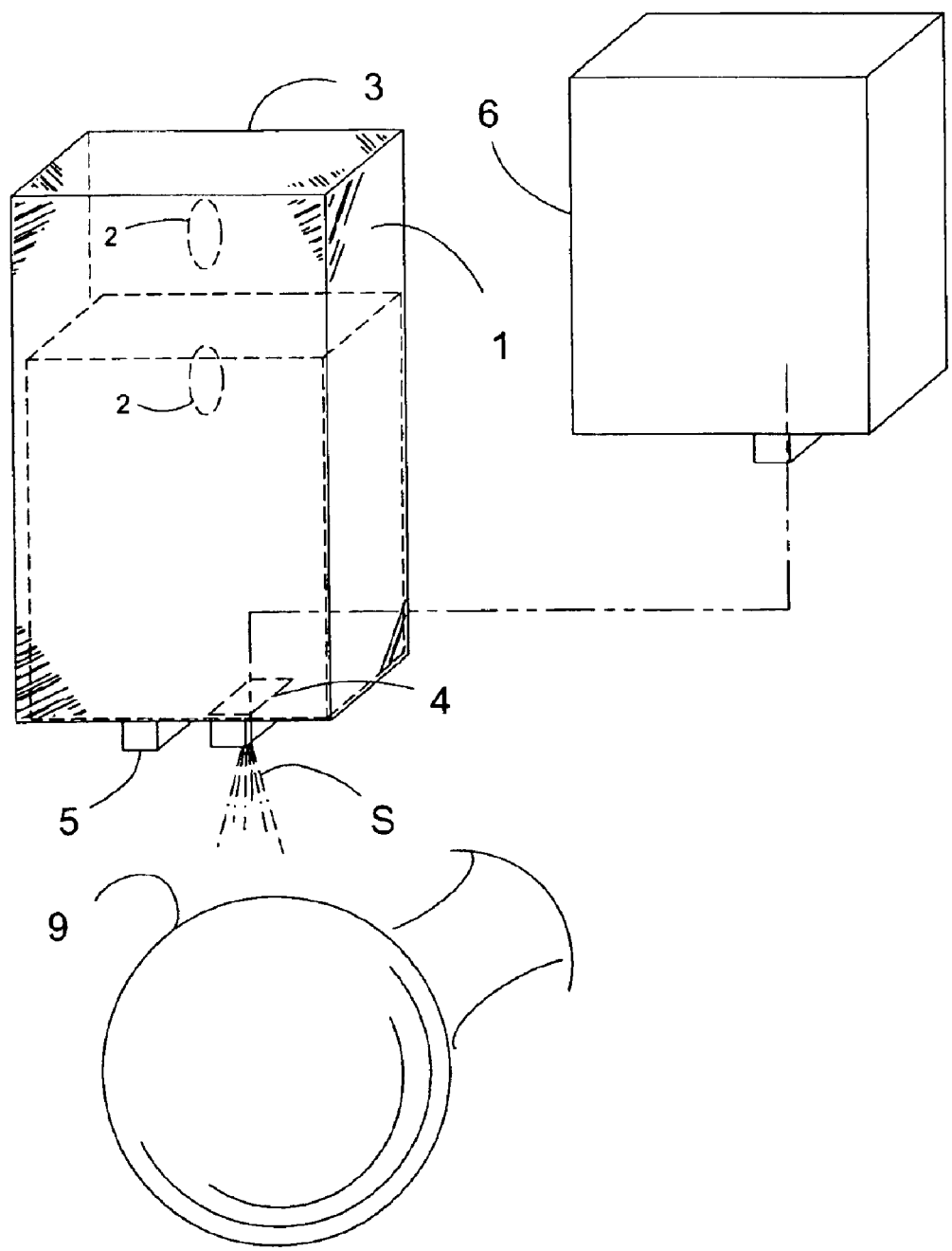
FIG. 1 is a schematic drawing of the device according to the invention.

FIG. 1 schematically illustrates the components of a preferred embodiment of the device for disinfecting door knobs or handles. The device consists of a housing 3 that is adapted to contain a soap or disinfectant (hereinafter referred to as "disinfectant") vessel 6 and a pump and battery compartment 1. The housing 3 may contain a hole or holes 2 to facilitate mounting the device on a door. In this case the holes should be of sufficient size to receive mounting screws. Other common ways of mounting the housing to the door may also be employed, e.g., double backed tape, straps, Velcro and glue. In some cases it may also be possible to hang the housing from the top of the door.

The disinfectant vessel 6 is designed to fit within the housing and to contain sprayable liquid disinfectant. The vessel may be permanently mounted in the housing as long as it contains provision for refilling when it is empty. In a preferred embodiment, however, the vessel will be removable and disposable, so that when it is empty, it can be discarded and replaced with a new or refilled one. In the embodiment of the invention illustrated in FIGS. 1, 2 and 3, the device will contain at least one rotatable and adjustable spray nozzle 7 adapted to aerosolize the liquid disinfectant and spray the resulting aerosol. In this case, the rotatable spray nozzle is designed to fit within the housing open port 4, thus allowing the spray to reach through the exterior of the housing. In another embodiment, illustrated in FIG. 4, the open port may be utilized to pass through tubing or pipe 12 connected to the electrically operated pump and spray nozzles located outside the housing. In this case it will not be necessary for the device to be equipped with a rotatable nozzle.

Figure 5:
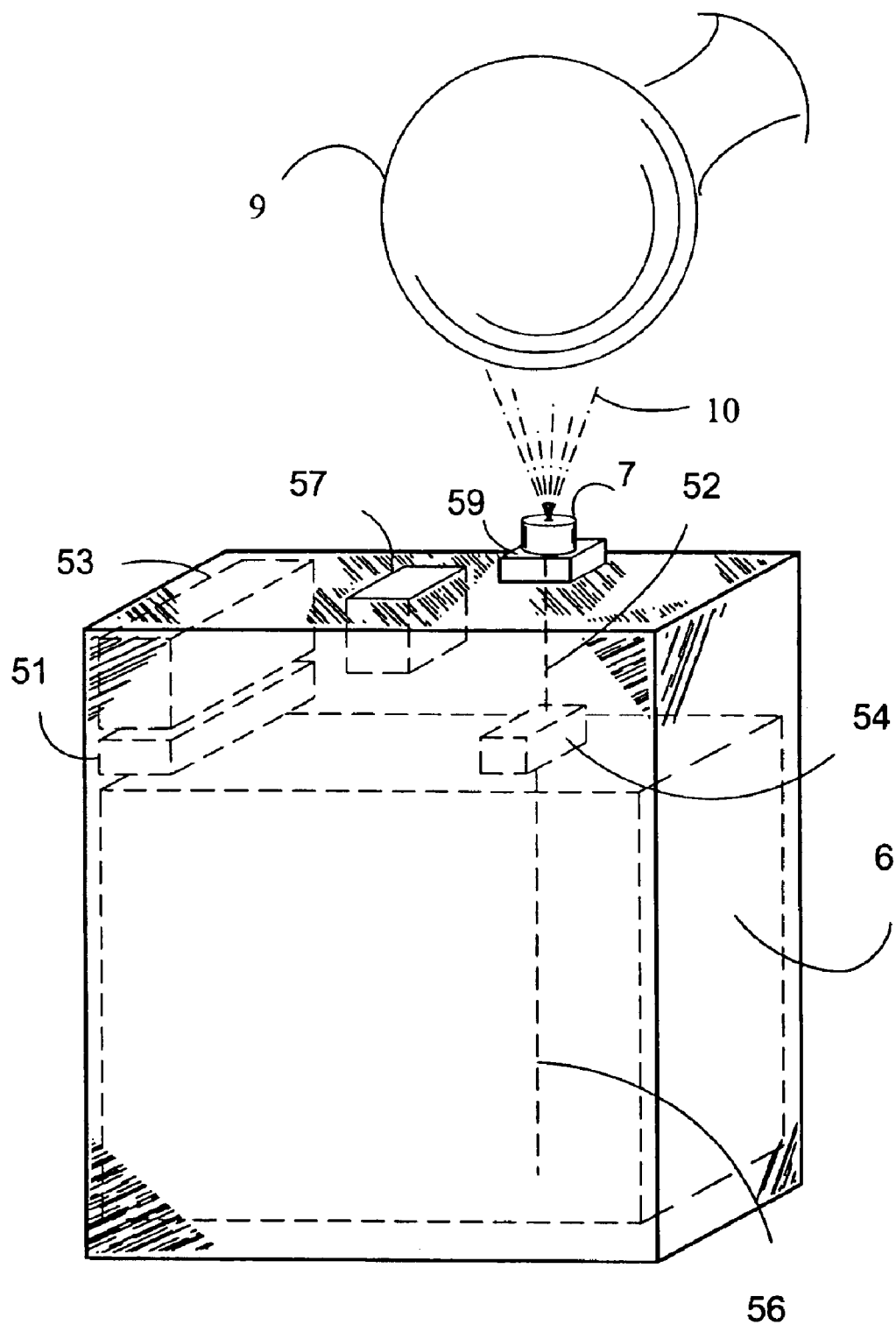
FIG. 5 is a schematic diagram of another preferred embodiment of the novel disinfecting device according to the present invention.

FIG. 5 illustrates another preferred embodiment of the novel device. In the figures like parts are identified by identical reference numbers. In this embodiment the spray nozzle 7 is oriented vertically above the disinfectant-containing vessel 6. Therefore, the device should be positioned on the door below or alongside the handle to be disinfected. An advantage to a horizontally aimed spray is that it minimizes the possibility of the spray shooting upward into a person's eyes, or downward onto a small child. FIG. 5 further shows that the nozzle 7 is connected to the liquid in vessel 6 in series by a supply tube 52, pump 54, and dip tube 56. When activated by controller 51 operating in conjunction with signals provided by sensor 57, and energized by power source 53, suction of pump 54 accepts liquid disinfectant via dip tube 56 and forces the liquid through supply tube 52 into nozzle 7. There the liquid mixes with air introduced through an intake port provided for that purpose (not shown) to form an aerosol spray.

The housing may also contain a locking capability 59 (FIG. 5) such that the spray nozzles mounted on the housing can be locked into a predetermined position to optimize the position of the spray on the knob or handle. As an example the spray nozzle may be mounted on a ball-type joint so that once the housing is mounted on a door in proximity to the knob, the nozzle can be moved to position the spray for optimum application to the knob. The nozzles can be caused to lock into position for example by providing detents or discrete slots place at different angles around the range of rotation of the nozzle. Thus the nozzle could be confined in one of these detent positions closest to the optimum spraying position.

In order to actuate the spraying of disinfectant, the housing will also contain in the pump and battery compartment 1 (FIG. 1) an electrically operated pump that is connected to a source of electrical energy. The source of electrical energy, which preferably is a removable battery, may also be contained within the pump and battery compartment. The pump will be connected to the rotatable and adjustable spray nozzle in such manner that when the pump is electrically energized, it will pump the liquid disinfectant through the spray nozzle or nozzles.

A notable aspect of the device of the invention is the handle operation sensor 5 mounted on the exterior of the housing. This sensor is effective to detect in real time whether the handle of the door is currently being manipulated by a human hand. In one embodiment the handle operation sensor is a motion detector positioned to continuously scan the door handle. When a user reaches and touches the door handle, the hand breaks the sensing beam of the detector. Usually, the hand remains in motion while manipulating the handle. Thus the sensor can send a "handle-in-use" signal to the device controller when motion in the sensing beam is detected and a "handle-not-used" signal when no motion is detected. In another embodiment, the handle operation sensor can be a proximity detection type sensor. That is, it detects a beam of suitable type in the region of the handle. When the beam is broken by the presence of a hand, the proximity sensor sends an appropriate signal to the device controller.

The sensor is electrically powered, and may receive its power from the same battery used to power the pump. A preferred sensor is a photoelectric cell or "electric eye". The sensor is also in electrical contact with the pump through the device controller. The controller can have a time delay circuit such that when the device detects manipulation of the handle by a hand, it does not trigger the pump usually for at least about one second, preferably about two seconds. This arrangement allows a hand to be removed from a door knob or handle before the spraying of disinfectant is starts.

Figure 2:
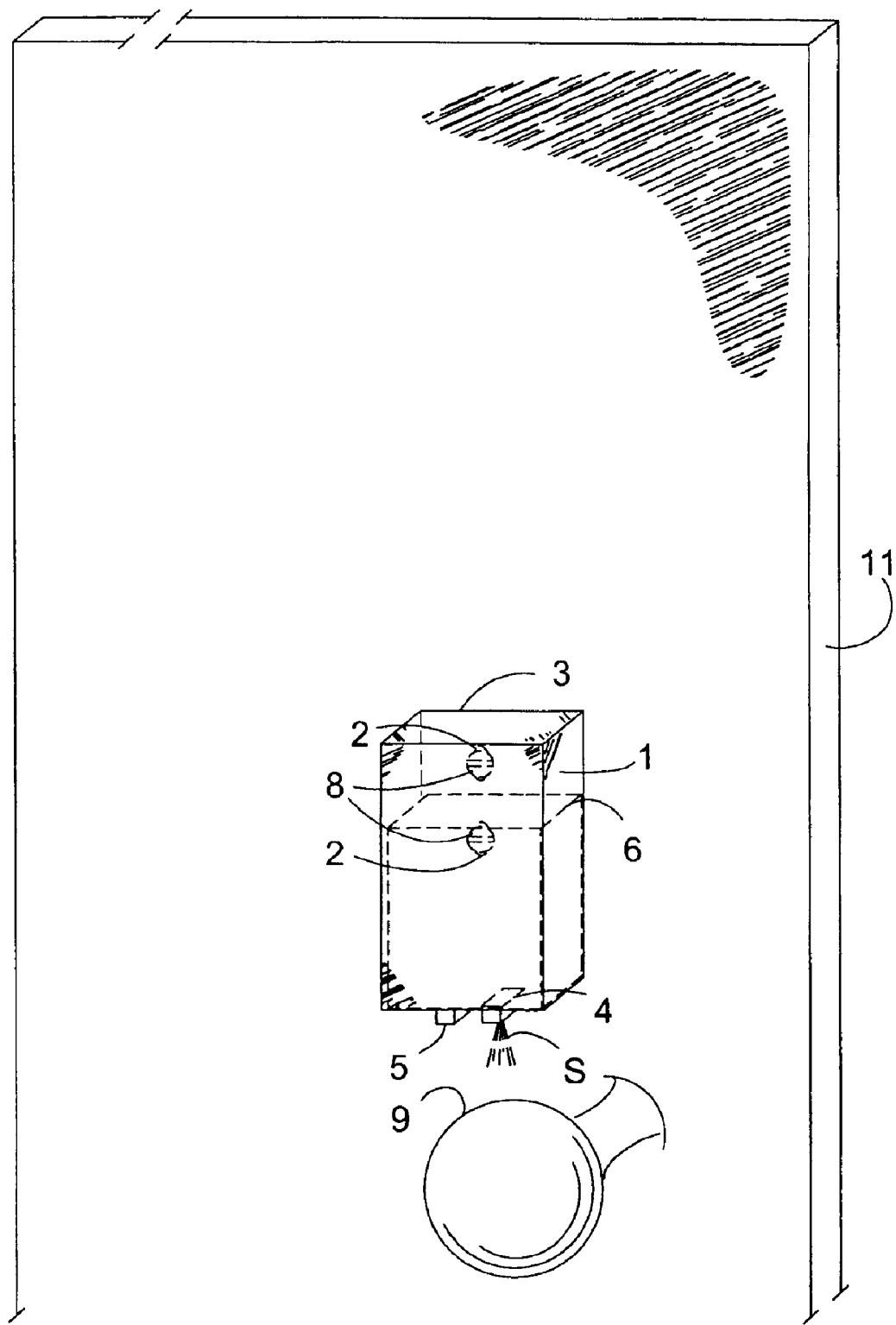
FIG. 2 is front view of the device according to the invention mounted on a door containing a door knob.
Figure 3:
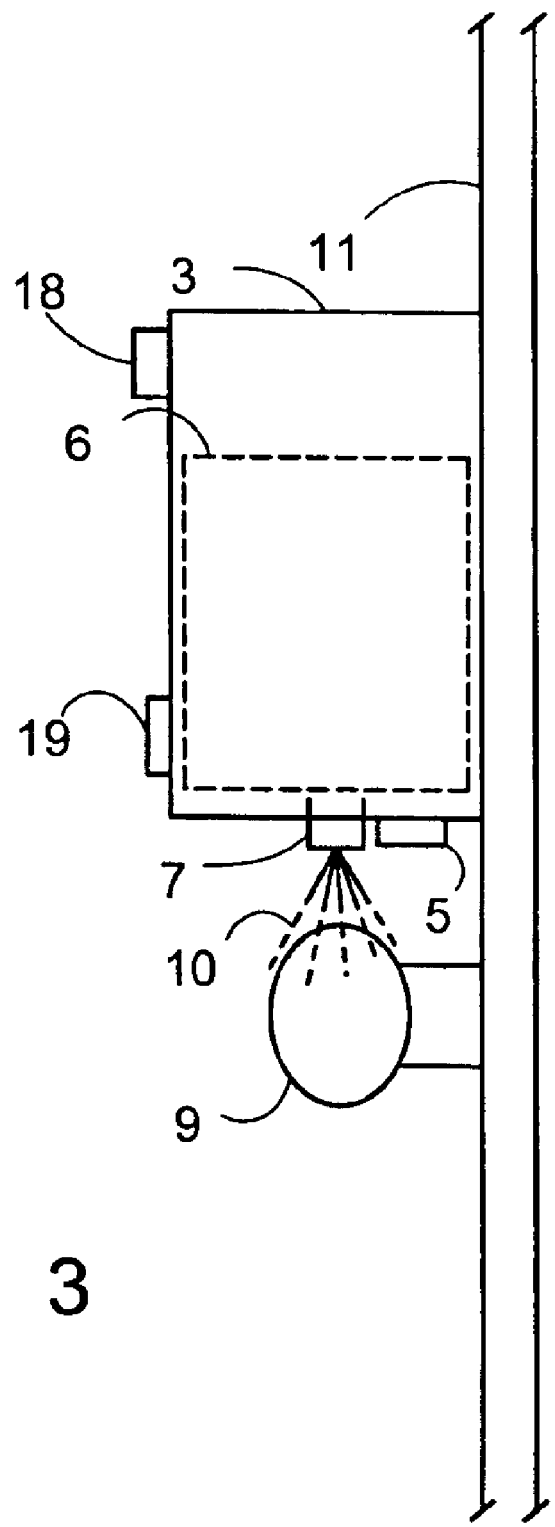
FIG. 3 is a side view of the device according to the invention mounted on a door containing a door knob.

In a preferred mode of operation, the device is mounted on a door as illustrated in FIG. 2 or 3, with the sensor trained on the door knob. The user grabs the door knob such that the hand breaks the sensor detection beam. The hand is then withdrawn, allowing the beam to return to the unbroken state. After a fixed delay time (typically a few seconds) the controller activates the pump to cause the disinfectant to be sprayed onto the knob or handle through the spray nozzles, which are preferably adapted to spray the material in the form of an aerosol. The time delay is provided so that the user's hand may be withdrawn before the spray occurs.

FIG. 2 schematically illustrates the use of the device of the invention on a door 11 containing a door knob 9, the mounting being accomplished by the use of screw fasteners 8. FIG. 2 also illustrates the spray pattern 10 produced by spray nozzle 7 impinging on the door knob 9. FIG. 3 is a side view of the same construction.

Figure 4:
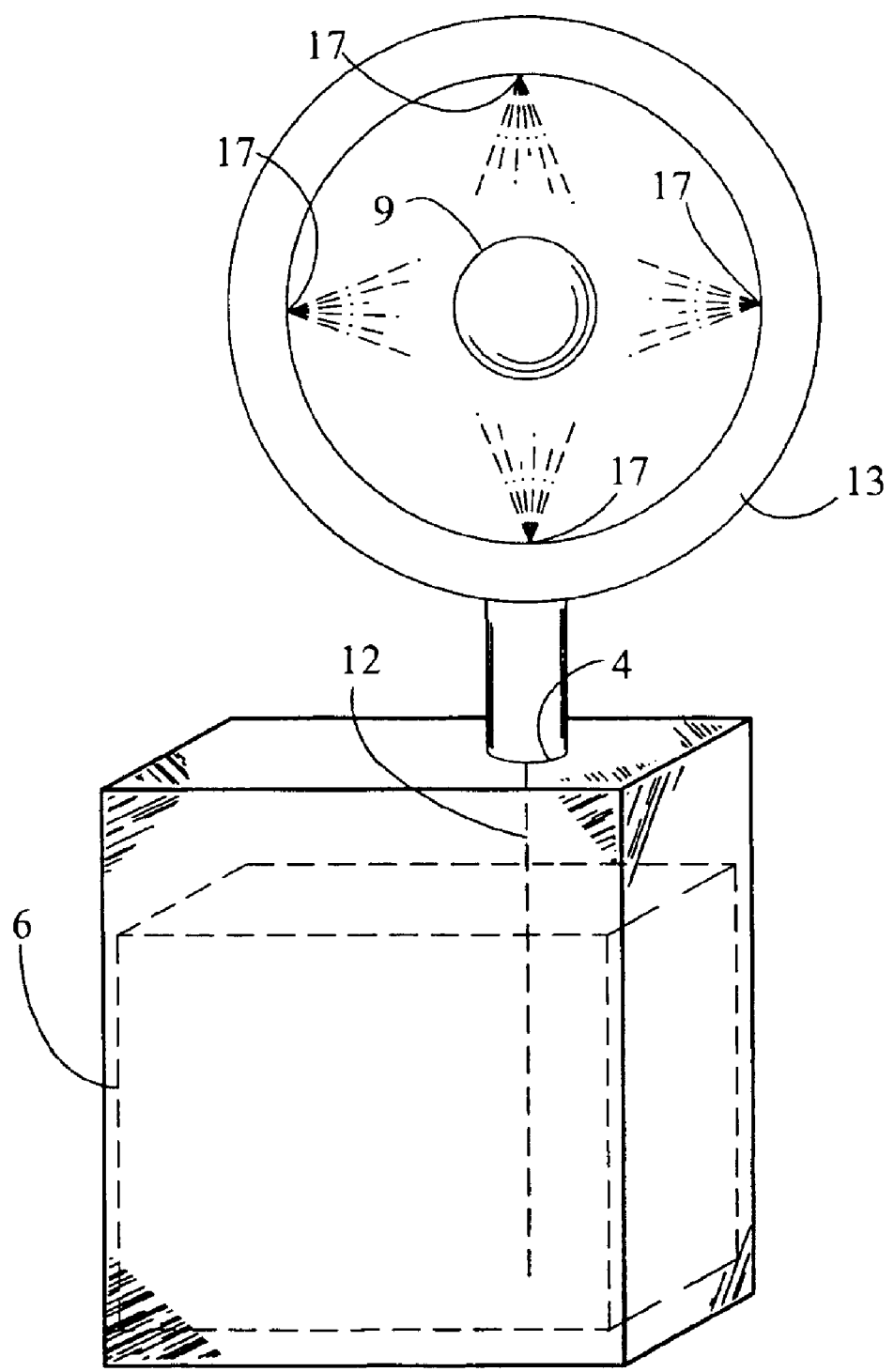
FIG. 4 is a schematic drawing of the device having spray nozzles in a ring encircling a door knob.

In another embodiment of the invention, illustrated in FIG. 4, a number of nozzles 17 are mounted in an adapter 13. The adapter shape is that of a ring encircling a door knob 9. In this case, the fluid flows from the reservoir 6 through a tube 12 of suitable length passing through a housing open port 4 to the ring 13. The ring has two or more spray nozzles 17 that encircle the knob and direct spray onto it from several angles. The spray nozzles may be equipped with a locking capability such that the spray nozzles mounted on the ring can be locked into a predetermined position to optimize the position of the spray on the knob or handle. In other contemplated embodiments, the adapter for multiple spray nozzles can have other shapes, such as a U-shape with the nozzles disposed on the legs of the U-shaped adapter to direct the spray toward the handle from different directions and thereby increase the surface contact of the disinfectant. A U-shaped adapter is preferred for elongated door handles.

Preferably, the disinfectant material is a bactericide and/or a virucide (i.e. an agent active against bacterial or viral infections). The material is preferably mixable with a liquid diluent, e.g. water, such that the resulting mixture can be aerosolized. Moreover, the diluent is preferably volatile at room temperature such that after the mixture settles on the environmental surface to be sanitized, the diluent can evaporate leaving a dry-to-touch surface. Any of a wide variety of bactericide and virucides well known in the art having the characteristics just described will be useful in the invention. Typical examples are 0.3% Triclosan®, Lysol®, and aqueous hypochlorite solutions. Preferred are Triclosan® and Lysol®.

The novel disinfecting device includes a controller which regulates the timing of the disinfecting sprays. The controller receives signals from the device sensors and then switches power on and off to energize and de-energize the pump such that appropriate disinfectant is sprayed onto the handle. It is contemplated that the controller includes a digital electronic processor unit programmed to accomplish the functions of the device. The control program can be tuned to optimize disinfecting in any particular situation by loading control parameters through software. For example, the duration of the spray should be long enough to adequately disinfect the handle. However, the spray should be as short as possible to conserve the inventory of disinfectant in the vessel and to permit the handle to dry quickly. Typically, the disinfecting spray will be from about 0.5 to about 10 seconds. The time delay between the time that the sensor detects operation of the door handle and when the disinfecting spray starts, mentioned above, can also be varied by loading the time delay value into the controller program through software.

In another mode of operation the controller can be configured to provide a maintenance spray at a preset, fixed amount of time after the most recent previous spray. This ensures that the surface is always adequately treated with disinfecting agent. Thus, every time that a handle-triggered spray occurs, the maintenance spray time delay is reset to the fixed amount of time. If no motion-triggered spray occurs, there will be a maintenance spray after each occurrence of the preset amount of time. The maintenance spray interval is preferably from about 30 minutes to about 4 hours and the value can be loaded into the controller program through software.

The controller can also be programmed with a clock and calendar function to automatically de-activate the disinfecting spray feature for blocks of time, for example for hours when the door is out of service, such as closed hours, weekends, holidays and the like. It is also contemplated that the control system for the novel device can include an optional battery reserve power sensor and indicator, such as a light emitting diode lamp, to provide an external signal that the battery should be replaced. The device can optionally have a fluid reservoir inventory sensor and external indicator to alert that the reservoir level is low and should be replenished.

A refinement to the modes of operation provides a proximity sensor 18 (FIG. 3) directed at the body of the user (i.e., perpendicular to the plane of the door). This proximity sensor sends a signal to the controls indicating that there can be no spray while the user is within a fixed, preset distance of the door. This mode of operation would prevent the user's hand being sprayed as it was about to be put on the door knob. Alternatively, the sensor can be set to stop any spray that is triggered to occur while a hand breaks the beam in reaching for the knob. This might occur, for example when a first person handles the knob and exits triggering a spray, e.g. 10 seconds later, and then a second person approaches, e.g. 8 seconds after the first person leaves, and reaches for the knob just as spraying commences. The control immediately stops the triggered spray, and restarts the motion triggered spray control sequence when the second person removes his hand from the beam. Yet another way to avoid user's hand being sprayed as it is on or about to be on the door knob is to provide a light and/or audible alarm 19 (FIG. 3) on the face of the housing that lights when the spray is on, or slightly before the spray starts.

It should be noted that although the invention has been illustrated for door knobs, it may also be utilized on doors containing fixed handles, such as for example sliding glass doors, many of which have vertically disposed handles. Furthermore, the invention is not only limited do door handles and knobs, but can also be used to disinfect faucets or spigot handles, particularly in wash stations located in high traffic areas such as for example, restaurants, hospitals, medical and dental offices, food preparation areas, day care facilities.

Although specific forms of the invention have been selected for illustration in the drawings and the preceding description is drawn in specific terms for the purpose of describing these forms of the invention fully and amply for one of average skill in the pertinent art, it should be understood that various substitutions and modifications which bring about substantially equivalent or superior results and/or performance are deemed to be within the scope and spirit of the following claims.

What is claimed is:

1. A device for disinfecting a handle of a door comprising:

a) a housing adapted to be mounted on the door, b) a source of electrical energy operative to supply power to the device, c) a vessel in the housing, adapted to contain a liquid comprising soap or disinfectant material, d) a handle operation sensor in the housing effective to detect whether the handle is in current operation by a human hand, e) a nozzle adapted to form an aerosol of the liquid and a spray of the aerosol onto said door handle, f) an electrically powered pump in the housing and being operative to pump the liquid from the vessel to the nozzle, g) a controller effective to activate and deactivate the pump, and h) an alarm perceptible by a human, in which the controller is configured to energize the alarm during a preselected lead-time immediately prior to each activation of the pump.

2. The device of claim 1 in which the nozzle is adjustable to form the spray in a range of directions relative to the housing.

3. The device of claim 2 further comprising a lock adapted to fix the direction of the spray.

4. The device of claim 1 which comprises a plurality of nozzles outside the housing and positioned to provide a plurality of sprays directed toward the handle from different directions.

5. The device of claim 1 wherein the handle operation sensor is a photoelectric cell.

6. The device of claim 1 wherein the source of electrical energy is a battery.

7. The device of claim 1 in which the handle operation sensor is adapted to generate a handle operation signal for use by the controller.

8. The device of claim 7 in which the controller comprises a program configured to utilize the handle operation signal to prevent activation of the pump when the handle is in operation by a hand.

9. The device of claim 7 in which the handle operation signal indicates that the handle is not currently in operation by a hand and in which the controller comprises a handle-in-use triggered delay which is operative to postpone activation of the pump until immediately after a preselected elapsed time following generation of the handle operation signal.

10. The device of claim 1 in which the controller comprises a maintenance spray program configured to activate the pump at expiration of a preset amount of time after a most recent previous spray.

11. A device for disinfecting a handle of a door comprising:
   a) a housing adapted to be mounted on the door,
   b) a source of electrical energy operative to supply power to the device,
   c) a vessel in the housing, adapted to contain a liquid comprising soap or disinfectant material,
   d) a handle operation sensor in the housing effective to detect whether the handle is in current operation by a human hand,
   e) a plurality of nozzles outside the housing adapted to form an aerosol of the liquid and positioned to provide a plurality of sprays onto the handle from different directions,
   f) an electrically powered pump in the housing and being operative to pump the liquid from the vessel to the nozzles, and
   g) a controller effective to activate and deactivate the pump,
in which the nozzles are on a hollow manifold mounted on the door circumferentially around the handle, the manifold having a bore operative to conduct the liquid to the nozzles, and which device further comprises a tube in fluid communication between the pump and the bore.

12. The device of claim 11 in which the manifold has a ring shape.

13. A device for disinfecting a handle of a door comprising:
   a) a housing adapted to be mounted on the door,
   b) a source of electrical energy operative to supply power to the device,
   c) a vessel in the housing, adapted to contain a liquid comprising soap or disinfectant material,
   d) a handle operation sensor in the housing effective to detect whether the handle is in current operation by a human hand,
   e) a nozzle adapted to form an aerosol of the liquid and a spray of the aerosol onto said door handle,
   f) an electrically powered pump in the housing and being operative to pump the liquid from the vessel to the nozzle,
   g) a controller effective to activate and deactivate the pump, and
   h) a proximity sensor directed outward from the door and being adapted to provide a proximity signal indicative that a person is located within a predefined distance of the door.

14. The device of claim 13 in which the controller is operative to prevent activation of the pump while a person is detected to be currently within the predefined distance.

15. A method of disinfecting a handle of a door comprising the steps of:
   (I) providing a device comprising a) a vessel containing a liquid comprising soap or disinfectant material, b) a handle operation sensor effective to detect whether a human hand is currently operating the handle, c) a nozzle adapted to form an aerosol of the liquid, and d) a controller effective to start and stop flow through the nozzle,
   (II) continuously scanning the handle by the handle operation sensor,
   (III) transmitting to the controller a handle-in-use signal while the sensor detects that the handle is currently being manipulated by a human hand and a handle-clear signal while the sensor detects that the handle is currently not being manipulated by a hand,
   (IV) spraying the aerosol from the nozzle onto the door handle for a preselected duration after each time that the controller first receives a handle-clear signal,
   (V) stopping the spraying at all times that the controller receives a handle-in-use signal,
   (VI) controlling the device to spray at expiration of a preset amount of time after most recent spraying has occurred, and
   (VII) providing a human perceptible alarm for a preselected lead-time immediately prior to commencing the spraying.

16. The method of claim 15 in which includes postponing of the spraying for a preselected handle-in-use triggered delay.

17. A method of disinfecting a handle of a door comprising the steps of:
   (I) providing a device comprising a) a vessel containing a liquid comprising soap or disinfectant material, b) a handle operation sensor effective to detect whether a human hand is currently operating the handle, c) a nozzle adapted to form an aerosol of the liquid, and d) a controller effective to start and stop flow through the nozzle,
   (II) continuously scanning the handle by the handle operation sensor,
   (III) transmitting to the controller a handle-in-use signal while the sensor detects that the handle is currently being manipulated by a human hand and a handle-clear signal while the sensor detects that the handle is currently not being manipulated by a hand,
   (IV) spraying the aerosol from the nozzle onto the door handle for a preselected duration after each time that the controller first receives a handle-clear signal, and
   (V) stopping the spraying at all times that the controller receives a handle-in-use signal,
   in which the device further comprises a proximity sensor directed outward from the door, and in which the method further comprises continuously scanning with the proximity sensor a space within a predefined distance from the door, detecting whether a person is currently within the space and preventing the spraying while the person is currently within the space.

* * * * *